United States Patent [19]

Lin et al.

[11] Patent Number: 5,536,859

[45] Date of Patent: Jul. 16, 1996

[54] ALPHA-OLEFIN CATALYST AND PROCESS

[75] Inventors: Kaung-Far Lin; Carroll W. Lanier, both of Baton Rouge, La.; William B. Waites, Orangeburg, S.C.

[73] Assignee: Amoco Corporation, Chicago, Ill.

[21] Appl. No.: 395,000

[22] Filed: Feb. 27, 1995

[51] Int. Cl.$^6$ .................. C07F 5/06; C07C 2/88
[52] U.S. Cl. ................ 556/190; 556/187; 585/637
[58] Field of Search .................... 556/187, 190; 585/637

[56] References Cited

U.S. PATENT DOCUMENTS

| | | | |
|---|---|---|---|
| 3,328,446 | 6/1967 | Poe et al. | 260/448 |
| 3,829,520 | 8/1974 | Ferrell | 260/677 |
| 5,049,687 | 9/1991 | Abazajian | 556/190 |
| 5,210,338 | 5/1993 | Samsel | 568/911 |
| 5,274,153 | 12/1993 | Allen et al. | 556/187 |
| 5,276,220 | 1/1994 | Samsel et al. | 568/911 |

*Primary Examiner*—Porfirio Nazario-Gonzales
*Attorney, Agent, or Firm*—Stephen L. Hensley

[57] ABSTRACT

This invention provides an improved process for the preparation of an aluminum alkyl chain growth product by the chain growth reaction of alpha-olefins on aluminum alkyl, the improvement comprising catalyzing the chain growth reaction that is a partially oxidized aluminum alkyl.

4 Claims, No Drawings

ALPHA-OLEFIN CATALYST AND PROCESS

FIELD OF THE INVENTION

This invention relates generally to the preparation of aluminum alkyls by the chain growth reaction of a lower olefin, especially ethylene, with a lower molecular weight alkyl aluminum and more specifically to an improved chain growth process using a catalyst that is a partially oxidized aluminum alkyl.

BACKGROUND OF THE INVENTION

Organoaluminum compounds have been previously utilized in the preparation of catalysts such as Ziegler-type catalysts. These catalysts preparations are based on the ability of organoaluminum compounds to act as reducing agents, i.e., reducing a transition metal to the zero valence state, e.g., U.S. Pat. No. 3,113,986.

U.S. Pat. No. 2,959,607 discloses the preparation of aluminum alkyls which contain at least one n-octyl group by subjecting octene-2 to the action of at least a stoichiometric amount of triisobutyl aluminum in the presence of a cobalt chloride catalyst at substantially atmospheric pressure. The catalyst apparently acts as both an isomerization and displacement catalyst in this process. The aluminum alkyls can be oxidized and hydrolyzed to make octanol-1.

U.S. Pat. No. 2,962,513 discloses a process for forming longer chain aluminum alkyls by a catalyzed olefin displacement of ethylene from ethyl aluminum compounds using a 100 to 300 percent stoichiiometric excess of $C_3$ or higher alpha-olefins.

The process uses salts and oxides of Group VIII metal as catalysts at temperatures of from about 50° to 200° C. at atmospheric pressure. Ethylene is evolved in the reaction.

U.S. Pat. No. 3,439,054 discloses a carbonyl catalyst that is useful for both hydrogenation of various unsaturated compounds as well as for causing isomerization in such compounds. The catalyst is dissolved as a mixture of transition metal carbonyl and an organoaluminum compound. This patent notes that organoaluminum compounds, such as alkoxides or halides, do not produce an active catalyst when used with the transition metal complex disclosed therein.

SUMMARY OF THE INVENTION

In accordance with this invention there is provided an improved process for the preparation of an aluminum alkyl chain growth product by the chain growth reaction of alpha-olefin on an aluminum alkyl, the improvement comprising catalyzing the chain growth reaction with a catalytically effective amount of a partially oxidized aluminum alkyl having the formula $$R'_n Al(OR'')_p$$

where R' and R" are the same or different and are individually $C_2$ to $C_{20}$ linear or branched alkyl, and the sum of n and p is 3.

Also provided is an improved process for the preparation of linear alpha-olefins by the chain growth reaction of alpha-olefin on an aluminum alkyl followed by olefin displacement of linear alpha-olefins from the aluminum chain growth product, the improvement comprising catalyzing the chain growth reaction with a catalytically effective amount of a partially oxidized aluminum alkyl having the formula $$R'_n Al(OR'')_p$$

where R', R", are alkyl as defined above, p is from 0 to 1 and the sum of n and p is 3.

The alpha-olefins of use in practicing this present invention are commercially available and can be made by the thermal cracking of paraffinic hydrocarbons or by the well-known Ziegler ethylene chain growth reaction and subsequent ethylene displacement on trialkyl aluminum. Individual olefins may be used as well as mixtures of such olefins. Examples of alpha-olefins suitable for chain growth include, but are not limited to, $C_2$ to $C_6$ straight chain alpha-olefins with ethylene being the preferred olefin.

The growth of alkyl chains on aluminum alkyls in accordance with the process of the invention is catalyzed by a trialkyl aluminum compound that is partially oxidized to form an alkyl aluminum alkoxide.

The alkyl aluminum alkoxide portion of the catalyst has the formula $$R'_n Al(OR'')_p$$

where R' and R" are alkyl as defined above, p is from 0 to 1 and the sum of n and p is 3.

The alkyl aluminum alkoxide is readily formed by the processes well known to those skilled in the art, i.e., by controlled oxidation of aluminum alkyl with, for example, air or by reaction with an aliphatic alcohol.

Aluminum trialkyl can be partially oxidized to the corresponding alkyl aluminum alkoxide by controlling the amount of oxygen supplied. For oxidation less than ⅔, the reaction between oxygen and alkyl trialkyl is quantitative. The exothermic oxidation reaction can proceed at about 100°–200° F. by bubbling air slowly under slight pressure (less than 5 bar). Extent of oxidation is controlled by the amount of oxygen in the air supplied to the aluminum trialkyl. For air oxidation, the molecular weight of alkyl aluminum alkoxide depends on the starting aluminum alkyl and extent of oxidation.

Alternatively, aluminum alkyl alkoxide can be prepared by the reaction between aluminum alkyl and alcohol with the formation of alkyl aluminum alkoxide and paraffin. In contrast to air oxidation, it is more flexible to adjust the molecular weight of alkyl aluminum alkoxide by alcohol oxidation. The molecular weight of alkyl aluminum alkoxide depends on the carbon number of alcohol, in addition to molecular weight of the aluminum alkyl and extent of oxidation. For a given aluminum alkyl and extent of oxidation, oxidation by alcohol is a practical way to adjust the molecular weight and hence the volatility of alkyl aluminum alkoxide. It will be shown later in some examples that premixing of alcohol with solvent and premixing of aluminum trialkyl with solvent is important to produce alkyl aluminum alkoxide. If appropriate premixing is not provided, some unstable aluminum compound other than alkyl aluminum alkoxide will be precipitated. Examples will be also shown to demonstrate both the lower volatility and higher thermal stability of alkyl aluminum alkoxide vs. aluminum trialkyl.

The chain growth reaction may utilize a neat partially oxidized aluminum alkyl medium or may utilize up to about 90 weight percent of a hydrocarbon solvent diluent such as ethane, propane, butane, pentane, hexane, heptane, octane, decane, and the like. Reaction temperatures may vary from approximately 100° to 200° C., with higher temperatures tending to increase olefinic and branched impurities. Pressures of ethylene may be varied from about 2000 psig to 4000 psig.

Ethylene chain growth at 2000–3000 psig, 120° C. to 140° C., 0.5 to 2 hours on the partially oxidized ethyl aluminum is carried out in a static mixer-reactor. The chain growth product is then subject to thermal ethylene displacement at 200–2000 psig, 250° C. to 350° C., 0.01 to 10 seconds in a static mixer-reactor. (Static mixers are not necessary for the process but may be used in both chain growth and displacement to maximize heat and mass transfer resistance.) Alternatively, catalytic displacement rather than thermal displacement may be used.

The ethylene chain growth product is formed and the ethyl aluminum alkoxide is regenerated. Separation of the olefins is readily accomplished by, for example, distillation due to the much higher boiling point of the partially oxidized aluminum alkyl catalyst compared to the olefin mixture. After separation, the catalyst is recycled for further chain growth.

The advantages of utilizing the partially oxidized alkyl aluminum compounds of the present invention for the production of alpha-olefins are numerous:

Alkoxide tends to be associated with other alkoxides (boiling points are thereby increased). Some difficult separations between olefins and trialkyl aluminum are replaced with the easy separation between olefins and the partially oxidized aluminum alkyl. Alkoxides are thermally more stable than alkyl.

A high carbon number alkoxide group can be obtained by reacting alkyl with a high carbon number alcohol. This will also make the alkoxide heavier and the separation easier.

More commercially acceptable olefins ($C_6$, $C_8$, $C_{10}$) are produced: Due to the almost perfect olefins/aluminum alkoxide separation, there is essentially no olefin in the recycle stream. This will limit heavy olefin formation in the chain growth reactor to that described by Poisson distribution. Heavy olefin formation in the ethylene displacement reactor is similarly reduced due to the absence of olefin in the feed to the displacement reactor.

Linear alpha-olefin quality (vinyl versus branched and internal) is greatly improved since much less olefins except ethylene are present in the feeds to the chain growth and displacement reactors.

The alkoxide group, which is attached to aluminum, acts as a heat diluent in the chain growth reactor due to its lesser reaction activity and high heat capacity. Even when no olefins are present in the recycle stream, no solvent is required for heat dilution. A judicial choice of percent oxidation and alkoxide chain length are needed for balance between reactivity for chain growth, heat transfer requirement for chain growth, and relative volatility for separation from olefins.

More efficient operation of the plant due to less recycle of olefins in the loop is achieved. Plant capacity is increased.

EXAMPLES

The following examples show the decreased volatility and increased thermal stability of alkyl aluminum alkoxide. Triethyl aluminum (TEA) is the model compound of the aluminum trialkyl chosen. N-octanol is the alcohol chosen for partial oxidation of TEA. N-tridecane is the inert solvent used for measuring relative volatility. Relative volatility of alkyl aluminum alkoxide will be less than reported in the following examples if heavier alcohols such as hexadecanol instead of n-octanol is used.

1. Triethyl Aluminum, No Oxidation 1000 g of n-tridecane is charged into a 3 liter round-bottom flask. 100 g of triethyl aluminum is then charged into the flask while its content is stirred at room temperature. The mixture is heated to 445° F. The vapor is condensed back to the flask by an overhead condenser to establish an equilibrium condition between the liquid and vapor at ambient pressure. Inert argon is purged up the line from the top of the overhead condenser. Two vapor condensate samples are taken and the aluminum contents are analyzed. The following data show that there is more aluminum in the vapor than in the initial feed, indicating that triethyl aluminum is more volatile than n-tridecane.

| Sample | Aluminum Content | Relative Volatility TEA/N-Tridecane |
| --- | --- | --- |
| Feed | 3.12 wt % | — |
| Condensate #1 | 5.53 wt % | 2 |
| Condensate #2 | 4.20 wt % | 1.4 |

Ten minutes after condensate #2 is taken, liquid in the still turns dark and black powder is formed. This indicates the thermal instability of TEA at 445° F. The still bottom liquid is at 445° F. for a total of 50 minutes before observing color change.

2. Triethyl Aluminum, 33% Oxidized by N-octanol

A total of 1000 g of n-tridecane, 100 g of triethyl aluminum and 114 g of n-octanol are mixed as follows: First, 114 g of n-octanol is premixed with 114 g of n-tridecane in a beaker at room temperature (1:1 weight ratio for n-octanol to n-tridecane). Then 100 g of triethyl aluminum is premixed with 886 g of n-tridecane in a dry box in the 3 liter glass flask at room temperature. The premixed n-octanol/n-tridecane is then poured slowly into the premixed triethyl aluminum/tridecane at room temperature while stirring. The temperature rises to 189° F. White crystals form throughout the liquid. This indicates that undesirable reactions between triethyl aluminum and n-octanol has occurred. The feed preparation procedure needs to be refined as in the next example to avoid white powder formation.

3. Triethyl Aluminum, 33% Oxidized by N-octanol

As in Example 2, a total mass of 1000 g of n-tridecane, 100 g of triethyl aluminum and 114 g of n-octanol are used. However, the mixing procedure is modified: First, 114 g of n-octanol is premixed with 228 g of n-tridecane in a beaker at room temperature (1:2 weight ratio of n-octanol to n-tridecane, instead of 1:1 in Example 2). Then 100 g of triethyl aluminum is premixed with 772 g of n-tridecane in the 3 liter glass flask in a dry box at room temperature. Then the premixed n-octanol/n-tridecane is poured slowly into the premixed triethyl aluminum/n-tridecane at room temperature while stirring over a four minute period. The temperature rises to 179° F. There is no white crystal formation and the solution is clear.

Similar procedure as in Example 1 is used to collect two vapor condensate samples under total reflux condition at 465° F. and 1 atmosphere. The results show that there is a tremendous reduction of aluminum in the vapor condensate. The very low relative volatility of 33% oxidized triethyl aluminum by n-octanol with respect to n-tridecane, in the range of 0.021 to 0.026, suggests that most of the liquid alkyl aluminum alkoxide in the equilibrium still exists as a dimer. The tendency for dimer formation of alkyl aluminum alkoxide is in general favored at high alkoxide content, low temperature and low solvent concentration.

| Sample | Aluminum Content | Relative Volatility 33% Oxidized TEA/N-Tridecane |
|---|---|---|
| Feed | 1.96 wt % | — |
| Condensate #1 | 0.061 wt % | 0.026 |
| Condensate #2 | 0.048 wt % | 0.021 |

In addition, the still bottom solution remains clear at reflux temperature 565° F. for 26 hours. After 26 hours, the run is terminated. This indicates the enhanced thermal stability of alkyl aluminum alkoxide.

4. Triethyl Aluminum, 25% Oxidized by N-octanol

A total mass of 1000 g of n-tridecane, 100 g of triethyl aluminum and 86 g of n-octanol is used to prepare the 25% oxidized alkyl aluminum alkoxide in a procedure similar to Example 3. However, the total reflux is conducted at 350° F. and 135 mm mercury pressure (under vacuum). Thee aluminum content in the vapor condensate and the relative volatility are shown below.

| Sample | Aluminum Content | Relative Volatility 25% Oxidized TEA/N-Tridecane |
|---|---|---|
| Feed | 1.99 wt % | — |
| Condensate #1 | 1.49 wt % | 0.72 |
| Condensate #2 | 1.61 wt % | 0.79 |

What is claimed is:

1. An improved process for the preparation of an aluminum alkyl chain growth product by the chain growth reaction of alpha-olefins on aluminum alkyl, the improvement comprising catalyzing the chain growth reaction with a partially oxidized aluminum alkyl.

2. The improved process according to claim 1 wherein the alpha-olefin is ethylene and the partially oxidized aluminum alkyl has the formula $$R'_n Al(OR'')_p$$

where R' and R" are the same or different and are individually $C_2$ to $C_{20}$ linear or branched alkyl, $0<p<1$ and the sum of n and p is 3.

3. In a process for the preparation of linear alpha-olefins by the chain growth reaction of an alpha-olefin in an aluminum alkyl followed by olefin displacement of linear alpha-olefins from the aluminum alkyl chain growth product, the improvement comprising catalyzing the chain growth reaction with a catalyst system which comprises a compound of the formula $$R'_n Al(OR'')_p$$

where R' and R" are the same or different and are individually $C_2$ to $C_{20}$ linear or branched alkyl, $0<p<1$ and the sum of n and p is 3.

4. In the process of claim 3 wherein the alpha-olefin is ethylene.

* * * * *

UNITED STATES PATENT AND TRADEMARK OFFICE
CERTIFICATE OF CORRECTION

PATENT NO.: 5,536,859

DATED: July 16, 1996

INVENTOR(S): Kaung-Far Lin, Carroll W. Lanier, William B. Waites

It is certified that error appears in the above-identified patent and that said Letters Patent is hereby corrected as shown below:

| Col. | Line | |
|---|---|---|
| 4 | 34-35 | "premixed triethyl aluminum/tridecane" should read --premixed triethyl aluminum/n-tridecane-- |
| 5 | 17-18 | "Thee aluminum content in the vapor condensate' should read --The aluminum content in the vapor condensate-- |

Signed and Sealed this

First Day of July, 1997

Attest:

BRUCE LEHMAN

Attesting Officer

Commissioner of Patents and Trademarks